United States Patent [19]

Cartwright

[11] 4,100,150

[45] Jul. 11, 1978

[54] STABILIZATION OF INTERFERON AGAINST MECHANICAL STRESS USING THIOCTIC ACID

[75] Inventor: Terence Cartwright, Merton, England

[73] Assignee: G. D. Searle & Co., Chicago, Ill.

[21] Appl. No.: 749,130

[22] Filed: Dec. 9, 1976

Related U.S. Application Data

[63] Continuation-in-part of Ser. No. 628,747, Nov. 4, 1975, abandoned.

[51] Int. Cl.² ............................................. A61K 45/02
[52] U.S. Cl. .................................. 260/112 R; 424/85
[58] Field of Search ....................... 260/112 R; 424/85

[56] References Cited

U.S. PATENT DOCUMENTS 3,981,991  9/1976  Stewart et al. ...................... 424/85

FOREIGN PATENT DOCUMENTS 2,549,768  5/1976  Fed. Rep. of Germany.

OTHER PUBLICATIONS

Nature, vol. 203, Sep. 1964, Fantes et al., pp. 1048–1050.
Nature, vol. 249, May, 1974, Stewart et al., pp. 460–461.
Proc. Soc. Exp. Biol. & Med. 146, 249–253 (1974), Edy et al.

Primary Examiner—Howard E. Schain
Attorney, Agent, or Firm—John J. McDonnell

[57] ABSTRACT

The present invention encompasses a method for stabilizing interferon during purification, concentration, packaging, filtering and storage comprising treating an interferon preparation with an effective stabilizing amount of reduced glutathione, thiodiglycol, thioethanolamine, thioalkanoic acid having 1–7 carbon atoms, monothioglycerol, dithiothreitol, thioctic acid, N-acetylcysteine, or N-acetyl-homo-cysteine, as a sulfur containing reducing agent for selectively retaining interferon thiols in the reduced state. The method of the present invention preserves the activity of interferon by selectively retaining interferon sulfhydryl (SH) functions in the reduced state without reducing interferon disulfide linkages (—S—S—) which are essential for activity, or by selectively blocking interferon sulfhydryl groups.

4 Claims, No Drawings

STABILIZATION OF INTERFERON AGAINST MECHANICAL STRESS USING THIOCTIC ACID

This is a continuation-in-part of my copending application Ser. No. 628,747, filed Nov. 4, 1975, now abandoned.

The present invention encompasses a method for stabilizing interferon during purification comprising treating an interferon preparation with an effective stabilizing amount of reduced glutathione, thiodiglycol, thioethanolamine, thioalkanoic acid having 1-7 carbon atoms, monothioglycerol, dithiotreitol, thioctic acid, N-acetylcysteine, or N-acetyl-homo-cysteine as a sulfur containing reducing agent for selectively retaining interferon sulfhydryl groups in the reduced state without reduction of essential disulfide linkages. The method of the present invention preserves the activity of interferon by selectively retaining interferon sulfhydryl (—SH) functions in the reduced state without reducing interferon disulfide linkages (—S—S—) which are essential for activity. Methods for producing and isolating interferon are extensively taught, Ciba Foundation Symposium-Interferon—edited by G. E. W. Wolstanholme and Maeve O'Connor; Little Brown and Co., Boston, 1967.

It is well known that interferon may be derived from cells grown in tissue culture and that cultures of non-transformed cells are preferred as a source of interferon. However, the interferon derived from such cells is highly susceptible to inactivation by mechanical stress, and other procedures involved in conventional purification of the material, and the yields of purified material obtained by these procedures are low.

It is known that interferon contains disulfide bonds which must remain intact if activity is to be maintained and reduction of these disulfide bonds with strong reducing agents destroys the activity of the interferon. However, it has now been shown that interferon also contains sulfhydryl groups and that these also are essential to the activity of the material. The process of inactivation, for example by mechanical stress described above probably involves either the linking together of the sulfhydryl groups or disulfide interchange reactions, to form inter or intra-molecular disulfide bridges, thereby causing the interferon to adopt a biologically inactive configuration.

Certain water soluble sulfur containing mild reducing agents retain interferon sulfhydryl groups in a reduced state without affecting disulfide linkages which are essential for interferon activity. The preferred reagents are: reduced glutathione (γ-L-glutamyl-L-cysteinylglycine), monthioglycerol, dithiothreitol, thioctic acid, N-acetylcystein, and N-acetyl-homo-cysteine. These compounds are represented by the following structures.

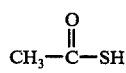

thioacetic acid, thioalkanoic acids having 1-7 carbon atoms are likewise suitable.

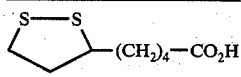 thioctic acid (1,2-dithiolane-3-valeric acid)

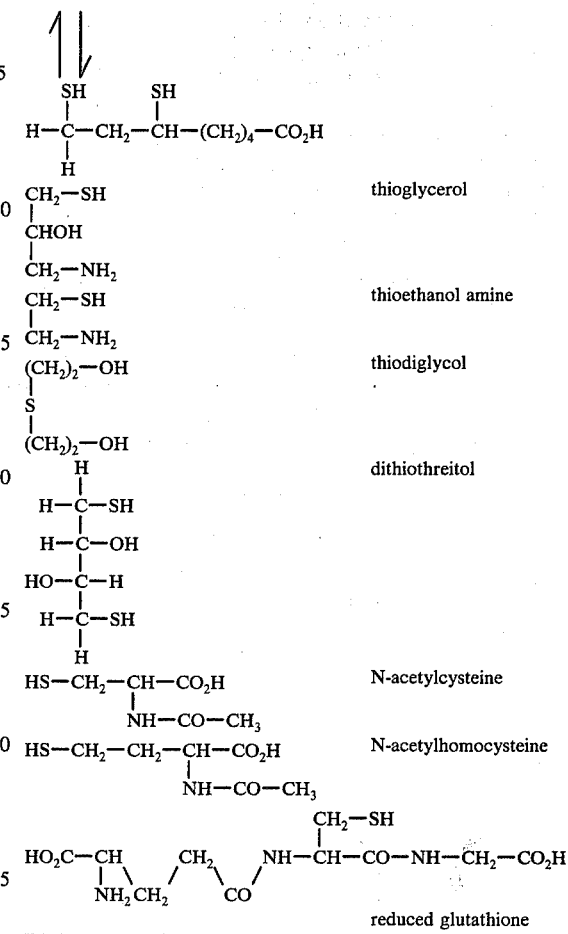

For purposes of the present invention an effective stabilizing amount is 0.1 to $10^{-4}$ molar concentration of the reducing agent in the solution containing interferon.

Preferred embodiments of the present invention are represented by the method of stabilizing fibroblast interferon against mechanical stress by treating an interferon preparation with at least $1 \times 10^{-4}$ moles per liter of thioctic acid, at least $1 \times 10^{-1.5}$ moles per liter of N-acetylcysteine, or at least $1 \times 10^{-2}$ moles per liter of dithiothreitol wherein the interferon concentration is 10 to $10^8$ units/ml.

Interferon derived from fibroblast cells is most preferably stabilized by treating the crude interferon preparation with at least $1 \times 10^{-4}$ moles per liter of thiotic acid before subjecting the interferon to mechanical stress such as ultra filtration, shaking, or precipitation. Thus, $10^{-4}$ moles per liter of thioctic acid effectively stabilize interferon solution having interferon titers of $10^4$ units/ml or in the range $10-10^8$ units/ml, more commonly $10^2-10^6$ units/ml.

It is to be particularly noted that related structures not having the requisite moiety reactive with sulphydryl groups are ineffective. For example, thioctic acid and thioalkanoic acids having 1-7 carbon atoms such as thioacetic acid are effective interferon stabilizing agents while octanoic acid is not. N-acetylcysteine is effective and N-acetylvaline is not.

The reagent, may be added to the crude preparation of interferon at the appropriate concentration (an effective stabilizing amount) and the interferon subsequently purified and concentrated by conventional techniques such as chromatography ultrafiltration or centrifugation. Upon completion of the purification the sulphydryl type of stabilizing agent may be removed by dialysis against a buffer solution which does not contain the agent.

Thus, the present invention encompasses an improved interferon preparation, the improvement of which comprises an interferon preparation containing about $10^{-4}$ moles per liter of thioctic acid, $1 \times 10^{-1.5}$ moles per liter of N-acetylcysteine or $1 \times 10^{-2}$ moles per liter of dithiotreitol. A preferred embodiment is an interferon preparation containing $10^{-3}-10^{-5}$, or $10^{-4}$ moles per liter of thioctic acid. Particularly preferred is an effective antiviral unit does of fibroblast interferon suitable for administering to an animal containing about $10^{-4}$ moles per liter of thioctic acid.

The following examples are illustrations of the present invention and should not be construed as limiting the invention in spirit or scope.

EXAMPLE 1

The ability of several compounds to prevent inactivation by mechanical stress of interferon derived from human fibroblasts is shown in Table 1 below:

TABLE 1

| Compound | Concentration(M) | Time of Agitation (Hours) | | | |
|---|---|---|---|---|---|
| | | 2 | 4 | 6 | 24 |
| | | Percentage remaining | | | |
| Control interferon | — | 30 | 20 | 10 | 3 |
| Thioctic acid | 1 mM | 100 | 100 | 100 | 95 |
| Octanoic acid | 1 mM | 30 | 20 | 10 | 3 |
| N-acetylcysteine | 100 mM | 90 | 85 | 85 | 80 |
| N-acetylvaline | 100 mM | 30 | 15 | 10 | 4 |
| Dithiothreitol | 10 mM | 90 | 90 | 85 | 85 |
| β-mercaptoethanol | 14 mM | 10 | 10 | 5 | 10 |

Samples of interferon in tissue culture medium are agitated by shaking in a tube 50 times per minute at a temperature of 4° C. The percentage of the original interferon activity remaining after increasing time intervals is given in Table 1. An indication that the reactive species involved the thiol group is given by the fact that octanoic acid and N-acetylvaline, which are closely chemically related to thiotic acid and N-acetylcysteine respectively, but lack the sulfhydryl moiety, are both totally inactive.

The strong reducing agent β-mercapthoethanol has no protective activity against the inactivation and itself caused inactivation of samples which are not agitated. β-mercaptoethanol is shown separately to disrupt disulfide bonds essential to the reactivity of interferon.

It is, therefore, demonstrated that only those preferred reagents which react with interferon sulfhydryl groups without disrupting disulfide bonds are able to stabilize interferon against mechanical inactivation. In contrast potent reagents which do disrupt the disulfide bonds of interferon cause a loss of activity of interferon even in the absence of physical stress.

EXAMPLE 2

Interferon from two types of fibroblast cells, MRC5 and FSA are subjected to increasing physical stress by shearing in a rotational viscometer comprising two concentric cylinders rotating in relation to each other.

The interferon had initial activity of 1000 u/ml.

RESULTS

| | | Activity of 1 Hour |
|---|---|---|
| unsheared control | | 1000 u/ml |
| FSA/$10^{-4}$ molar | thioctic acid | about 850 u/ml |
| MRC5/$10^{-4}$ molar | thioctic acid | about 700 u/ml |
| FSA sheared control | | about 250 u/ml |
| MRC5 shear control | | about 50 u/ml |

EXAMPLE 3

Samples of interferon 0.1 molar in N-acetylcysteine are shaken at the rate of 50 times per minute for a total period of 24 hours at 4° C. After 24 hours the N-acetylcysteine treated interferon samples have essentially unchanged activity and untreated controls have 1/10 the original activity after 24 hours of shaking.

EXAMPLE 4

Reagents of the present invention function by maintaining a reducing atmosphere around the critical sulfhydryl groups. They do not bind to these groups and their reaction is therefore reversible, if for example, they are dialysed out of the interferon preparation. Furthermore, interferon which is rendered unstable by dialysing away a reducing stabilizer may be restabilized by the addition of a fresh reducing agent.

The properties of reagents according to the present invention are illustrated by the examples described in Table 2. An aqueous preparation of interferon is subjected to treatment with various reagents and then agitated for 24 hours at 4° C. The resulting loss of total interferon activity as a result of this agitation is measured.

TABLE 2

| No. | Treatment | % Loss of Activity (shaking for 24 hours at 4° C) |
|---|---|---|
| 1 | None | 90 |
| 2 | 0.1 M N-acetylcysteine | 0 |
| 3 | As 2 above and dialysed | 93 |
| 4 | As 3 above then 0.1 N-acetyl cysteine | 0 |

EXAMPLE 5

A conventional procedure for concentration or purification of interferon is ultra filtration on a membrane. However, under conventional conditions much of the activity of the interferon is that derived from fibroblasts. It is shown in Table 3 below that interferon may be stabilized against such inactivation by treatment with 0.1 molar N-acetylcysteine.

TABLE 3

| Stabilizer | Ultrafiltration membrane | Concentration factor | % yield of activity |
|---|---|---|---|
| None | UM 10 | 5 | 20 |
| | UM 20 | 5 | 11 |
| 0.1 M N-acetyl cysteine | UM 10 | 5 | 100 |
| | Um 20 | 5 | 100 |

EXAMPLE 6

A further conventional purification procedure for interferon is salt precipitation using for instance increasing concentrations of ammonium sulfate or potassium thiocyanate at 4° C. at mildly acidic or neutral pH. Under conventional conditions much of the activity of interferon is lost in carrying out this procedure when the interferon is derived from fibroblasts. In Table 4 it is shown that interferon may be effectively stabilized in ammonium sulfate precipitation systems by addition of 1 mM thioctic acid.

TABLE 4
USE OF SULFHYDRYL STABILIZER IN INTERFERON PRECIPITATION BY AMMONIUM SULFATE AT pH 7.0 AT 4° C

| Treatment | Percent Yield |
|---|---|
| Unprotected interferon | 30% |
| Interferon plus 1 mM Thioctic acid | 100% |

Reversible treatment with a reducing agent whose reactivity is such that only those sulfhydryl groups which play a part in interferon inactivation are reduced and not the essential disulfide bonds stabilizes fibroblast interferon against the inactivation which typically occurs while undergoing conventional purification procedures.

EXAMPLE 7

Human fibroblast interferon is treated with $10^{-4}$ moles per liter of thioctic acid and stored at 4° C for 14 weeks. The stability of the thioctic acid treated interferon is compared to that of the control. The $\log_{10}$ of interferon titre remains substantially unchanged for the thioctic acid treated interferon while the interferon titre for untreated interferon falls from $10^{3.5}$ to $10^2$ after 14 weeks at 4° C. Thus thioctic acid in concentrations of $10^{-5}$ to $10^{-3}$ M preferably at least $10^{-4}$ molar prolongs the shelf life of fibroblast interferon solution having interferon titres of about $10^4$ units/ml.

What is claimed is:

1. A method for stabilizing interferon against mechanical stress conprising treating an interferon preparation with an effective stabilizing amount of thioctic acid for selectively retaining interferon sulfhydryl groups in the reduced state without reduction of essential disulfide linkages.

2. A method according to claim 1 for stabilizing interferon against mechanical stress comprising treating an interferon preparation with at least $1 \times 10^{-4}$ moles per liter of thioctic acid.

3. A method according to claim 1 wherein the interferon is derived from fibroblast cells.

4. An interferon preparation stabilized against mechanical stress comprising 10 to $10^8$ units/ml of interferon in combination with about $10^{-4}$ moles per liter of thioctic acid.

* * * * *